United States Patent
Betts et al.

(10) Patent No.: US 7,872,574 B2
(45) Date of Patent: Jan. 18, 2011

(54) SENSORY ENHANCEMENT SYSTEMS AND METHODS IN PERSONAL ELECTRONIC DEVICES

(75) Inventors: William L. Betts, St. Petersburg, FL (US); Carol Betts, St. Petersburg, FL (US)

(73) Assignee: Innovation Specialists, LLC, St. Petersburg, FL (US)

( * ) Notice: Subject to any disclaimer, the term of this patent is extended or adjusted under 35 U.S.C. 154(b) by 1388 days.

(21) Appl. No.: 11/345,058

(22) Filed: Feb. 1, 2006

(65) Prior Publication Data

US 2009/0085873 A1 Apr. 2, 2009

(51) Int. Cl.
G08B 1/08 (2006.01)
(52) U.S. Cl. .............. 340/539.26; 340/539.11; 340/539.24; 381/150; 704/226; 704/231
(58) Field of Classification Search ........... 340/539.26, 340/539.24, 539.11, 539.16, 539.28, 540, 340/601; 381/122, 150; 704/226, 231, 233, 704/258
See application file for complete search history.

(56) References Cited

U.S. PATENT DOCUMENTS

| | | | | |
|---|---|---|---|---|
| 4,640,134 A | 2/1987 | Simmons | ...................... | 73/648 |
| 5,216,541 A | 6/1993 | Takesue et al. | .............. | 359/561 |
| 5,703,321 A | 12/1997 | Feierlein et al. | ............. | 102/427 |
| 5,703,835 A | 12/1997 | Sharkey et al. | .............. | 367/124 |
| 5,970,446 A * | 10/1999 | Goldberg et al. | ............ | 704/233 |
| 6,009,320 A | 12/1999 | Dudley | ....................... | 455/404 |
| 6,173,074 B1 | 1/2001 | Russo | ......................... | 382/190 |
| 6,222,458 B1 | 4/2001 | Harris | ..................... | 340/568.1 |
| 6,232,882 B1 | 5/2001 | Hed et al. | .................... | 340/601 |
| 6,333,694 B2 * | 12/2001 | Pierce et al. | ............. | 340/573.1 |
| 6,434,372 B1 | 8/2002 | Neagley et al. | ............. | 455/106 |
| 6,466,958 B1 | 10/2002 | Van Wechel et al. | ........ | 708/422 |
| 6,587,824 B1 | 7/2003 | Everhart et al. | ............. | 704/275 |
| 6,638,407 B1 | 10/2003 | Peng | .......................... | 204/432 |
| 6,732,064 B1 | 5/2004 | Kadtke et al. | ............... | 702/189 |
| 6,826,762 B2 | 11/2004 | Shell et al. | ................... | 719/328 |
| 6,830,668 B2 | 12/2004 | Musho et al. | ............... | 204/400 |
| 6,856,253 B1 * | 2/2005 | Crook | ........................ | 340/632 |
| 6,876,968 B2 * | 4/2005 | Veprek | ........................ | 704/258 |
| 6,882,837 B2 | 4/2005 | Fernandez et al. | ........ | 455/404.1 |
| 6,943,667 B1 | 9/2005 | Kammer et al. | ........ | 340/286.01 |
| 6,944,466 B2 | 9/2005 | Bi et al. | .................... | 455/456.1 |
| 6,975,277 B2 | 12/2005 | Tran | ........................ | 343/792.5 |
| 7,109,859 B2 * | 9/2006 | Peeters | .................. | 340/539.11 |
| 7,457,750 B2 * | 11/2008 | Rose et al. | .................. | 704/244 |
| 7,574,451 B2 * | 8/2009 | Burges et al. | ...................... | 1/1 |
| 2004/0016104 A1 | 1/2004 | Mukundan et al. | ......... | 29/591.1 |
| 2004/0081582 A1 | 4/2004 | Brooke | ......................... | 422/62 |
| 2005/0123150 A1 | 6/2005 | Betts | ......................... | 381/94.3 |

* cited by examiner

*Primary Examiner*—Davetta W Goins
(74) *Attorney, Agent, or Firm*—Thomas, Kayden, Horstemeyer & Risley, LLP

(57) ABSTRACT

Disclosed are personal electronic devices (PEDs) having a sensory enhancement (SE) system for monitoring environmental conditions and detecting environmental events, for example but not limited to, changes in acoustic, thermal, optical, electromagnetic, chemical, dynamic, wireless, atmospheric, or biometric conditions. The detection of such events can be used to invoke a notification, an alert, a corrective action, or some other action, depending upon the implementation to the PED user or another party.

26 Claims, 7 Drawing Sheets

SENSORY ENHANCEMENT SYSTEMS AND METHODS IN PERSONAL ELECTRONIC DEVICES

FIELD OF THE INVENTION

The present invention generally relates to sensory enhancement (SE) systems and methods implemented in personal electronic devices (PEDs) for monitoring environmental conditions and detecting environmental events, for example but not limited to, changes in acoustic, thermal, optical, electromagnetic, chemical, dynamic, wireless, atmospheric, or biometric conditions. The detection of such events can be used to invoke a notification, an alert, a corrective action, communication to another device, or some other action, depending upon the implementation.

BACKGROUND OF THE INVENTION

Humans today live in a complex and rapidly changing environment. Frequently, they utilize and carry or otherwise transport with them one or more personal electronic devices (PEDs) that demand their attention and further increase the complexity of their environment. Personal digital assistants (PDA's), global positioning system (GPS) navigators, portable computers, calculators, digital cameras, hearing aids, radios, tape, CD, DVD, and/or MP3 players, video games, and wireless (e.g., cellular) telephones are good examples of PEDs.

The inventor has discovered that the functionality of such PEDs can be expanded to provide very beneficial sensory enhancement to the user with respect to the environment in which the PED is situated, as will be described in detail hereinafter.

SUMMARY OF INVENTION

The present invention provides various embodiments for sensory enhancement (SE) in a personal electronic device (PED). The present invention provides systems and methods that can detect acoustic, thermal, optical, electromagnetic, chemical, dynamic, wireless, atmospheric, or biometric signals in an environment to which the PED is exposed and generate appropriate notification signals. This sensory enhancement functionality may be implemented in its own PED or may be implemented in virtually any type of PED that performs other functions, for example but not limited to, a personal digital assistant (PDA); GPS navigator; portable computer; calculator; digital camera; hearing aid; radio; tape, CD, DVD, and/or MP3 player; video game; and wireless (e.g., cellular) telephone; etc. The conventional functions of these aforementioned PEDs are called herein "electronic based intelligence functions." In the preferred embodiments, sensory enhancement functionality can proceed concurrently with the electronic based intelligence functions of the PED.

One embodiment of a device for sensory enhancement, among others that are described herein, can be summarized as follows. The device is essentially a PED that can be transported with a user. It comprises a first means for performing a first electronic based intelligence function; and a second means for performing a second electronic based intelligence function. The second means comprises a transducer (or sensor), means for detecting an event in an environment to which the PED is exposed via the transducer, and means for producing a notification upon detection of the event.

Another embodiment of a device for sensory enhancement, among others that are described herein, can be summarized as follows. The device is essentially a PED that can be transported with a user. It comprises a means for storing a reference signature, a means for detecting an event in an environment associated with the PED and a means for producing a notification upon the detecting of the event. In this embodiment, the means for detecting includes a means for sensing a signal in the environment, a means for correlating the signal with the reference signature, and a means for indicating the detecting of the event based upon the correlating.

Another embodiment of a device for sensory enhancement, among others that are described herein, can be summarized as follows. In essence, this device includes functionality to permit it to cooperate with and exchange information with other PEDs so that measurement and detection functions can be enhanced. In a sense, a distributed system for sensory enhancement is thereby implemented.

Such an embodiment of the distributed system, among others that are described herein, can be summarized as follows: a plurality of PEDs; means for communicating among the plurality of PEDs a selection of a reference signature corresponding to an event to be detected; means for permitting one or more of the PEDs to measure a characteristic of an environment with a transducer associated therewith; means for detecting the event in one or more of the PEDs; and means for generating a notification signal in the one or more PEDs indicating detection of the event. Furthermore, although not necessary for implementation, in the preferred embodiment, the PEDs further include a means for permitting the users to define whether or not their respective PEDs will cooperate and exchange information with others.

An embodiment of a method for sensory enhancement, among others that are described herein, can be summarized as follows. The method comprises the steps of: communicating to a PED a selection of a reference signature corresponding to an event to be detected; transporting the PED into an environment; permitting the PED to measure a characteristic of the environment with the transducer associated with the PED; and receiving a signal from the PED indicating detection of the event.

Another embodiment of a method for sensory enhancement, among others that are described herein, can be summarized as follows. The method comprises the steps of: providing a plurality of PEDs; communicating among the plurality of PEDs a selection of a reference signature corresponding to an event to be detected; permitting one or more of the PEDs to measure a characteristic of an environment with a transducer associated therewith; detecting the event in one or more of the PEDs; and generating a notification signal in the one or more PEDs indicating detection of the event.

Other systems, methods, features, and advantages of the present invention will become apparent to one of skill in the art upon examination of the drawings and detailed description.

BRIEF DESCRIPTION OF THE DRAWINGS

The present invention can be better understood with reference to the following drawings. The components in the drawings are not necessarily to scale, emphasis instead being placed upon clearly illustrating the principles of the present invention. Like reference numerals designate corresponding parts throughout the several views.

DETAILED DESCRIPTION OF THE PREFERRED EMBODIMENT

Figure 1:
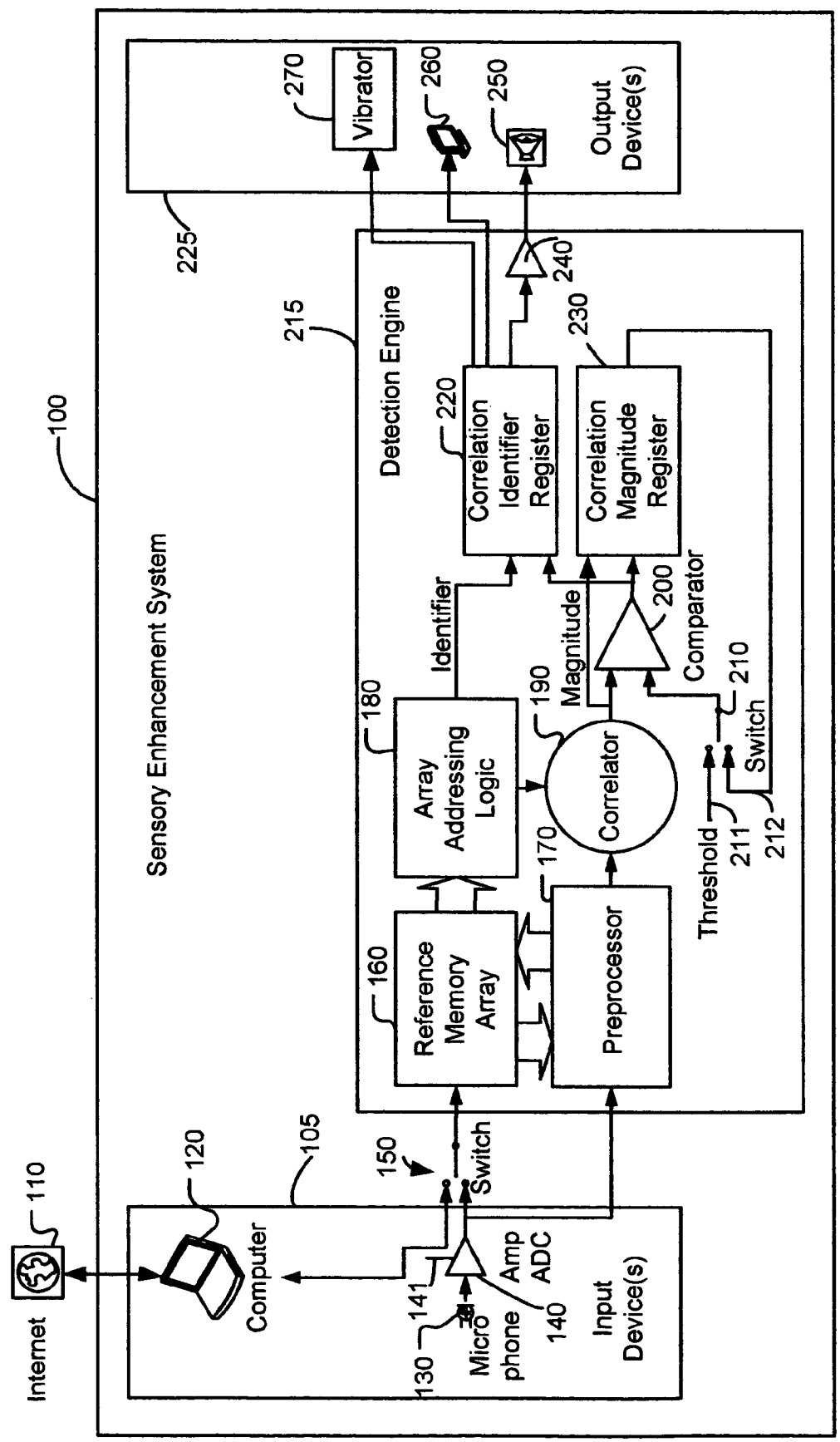
FIG. 1 is a block diagram of one example implementation of a sensory enhancement system.

FIG. 1 is a block diagram of an example implementation of the sensory enhancement (SE) system in accordance with the present invention and is generally denoted by reference numeral 100. As is shown in FIG. 1, the SE system 100 includes one or more input devices 105, such as but not limited to, a computer 120 as shown that can be communicatively coupled to the Internet 110, an audio microphone 130 as shown, etc., for receiving one or more reference signatures that are used to identify environmental events. The input devices 105 can be any transducer for sensing acoustic, thermal, optical, electromagnetic, chemical, dynamic, wireless, atmospheric, or biometric conditions (e.g., a body function, such as blood pressure, body temperature, heart rate, sugar level, heart beat, oxygen level, etc.), for example but not limited to, an audio microphone, video camera, Hall Effect magnetic field detector, flux gate compass, electromagnetic field detector, accelerometer, barometric pressure sensor, thermometer, ionization detector, smoke detector, gaseous detector, radiation detector, biometric sensor, etc.

The system 100 further comprises a detection engine 215 that stores the one or more reference signatures that are used to identify environmental events, that correlates sensed environmental signals with the reference signatures, and that detects occurrences of the environmental events. The detection engine 215 can be implemented in hardware, software, or a combination thereof, but is preferably implemented in software executed by a computer based architecture. When designed via software, it can be stored and transported in a computer readable medium. The system 100 further comprises one or more outputs 225, such as but not limited to, as shown, an audio speaker 250, a visual display device 260, a mechanical vibrator 270, etc., for advising of detection of environmental or physiological events.

The SE system 100 is designed to be operated in several modes. The architecture of the SE system 100 will be described as each of these modes is described in detail hereafter.

In a first mode, a computer 120 is connected to a reference memory array 160 by a switch 150. One or more reference signatures are collected by the computer 120 and loaded into the reference memory array 160.

Reference signatures, such as bird calls, a human voice, registered emergency signals (e.g., a police car siren or fire truck siren), etc. can be collected from the Internet 110 or another source by the computer 120.

As an example, bird songs can be acquired via download from the U.S. Geological Survey web site at http://www.mbr-pwrc.usgs.gov (Gough, G. A., Sauer, J. R., Iliff, M. *Patuxent Bird Identification Infocenter.* 1998. Version 97.1. Patuxent Wildlife Research Center, Laurel, Md.). For instance, the bird song associated with the Eastern bluebird (*Sialia sialis*) can be downloaded from this site and is a 4 second, 32 Kbps MPEG Audio Layer-3 recording. Another site that includes .mp3 audio recordings and sonograms of bird songs is http://askabiologist.asu.edu/expstuff/experiments/bird-songs/birds_az.html (Kazilek, C. J. Ask A Biologist web site, Arizona State University, 1997-2004). Sonograms are graphs of frequency versus time and can include a measure of intensity or amplitude by gray scale or color variation. The SE system 100 is designed to transform the audio recordings into suitable numerical arrays for recognition. The frequency range of 0.2 Hz to 20 KHz is sufficient for bird calls and speech recognition applications. Furthermore, a time interval of several seconds is normally sufficient.

The preprocessor 170 extracts the reference signals from the reference memory array 160 and reformats them to facilitate rapid correlation. The frequency domain is a preferred format for sonograms. The preprocessor 170 analyzes each signature by a sequence of Fourier transforms taken repeatedly over a period of time corresponding to the duration of the signature. The Fourier transform is preferably a two-dimensional vector, but a single measure of amplitude versus frequency is sufficient. In the preferred embodiment, the SE system 100 processes a 3-dimensional array of amplitude, frequency, and time. The transformed signature arrays are stored back into a reference memory array 160 for subsequent rapid correlation. Preferably, each reference signature array includes an identifier field associated with the signature. As an example, for a bird song identification, this may be the name and picture/image of the bird associated with the signature. Or, in the case of emergency signals, the identifier can simply be an indication of the type of emergency. Furthermore, the emergency identifier can also indicate an appropriate evasive or corrective action.

In a second mode of operation, system 100 can acquire the reference signature signal directly from the local environment via the audio microphone 130. Audio signals from the microphone 130 are amplified and converted to digital signals by amplifier and analog-to-digital converter (ADC) 140. The digital signal from amplifier and ADC 140 is selected by the user via the switch 150 and loaded directly into the reference memory array 160. Preferably, several seconds of signal are collected in this particular application. Then, the preprocessor 170 reformats the reference signal for rapid correlation, preferably by Fourier transform.

A gain control 141 associated with the ADC 140 can be controlled by the user to control the range of the microphone 130 (or another input device, if applicable, and depending upon the application).

In a third mode of operation, the SE system 100 monitors the environment continuously (at discrete successive short time intervals due to the computer-based architecture) for signals that match those stored in the reference memory array 160. To reduce computational burden, the preprocessor 170 is designed to monitor the microphone 130 for a preset threshold level of signal before beginning the correlation process. When the signal exceeds the preset threshold level, the preprocessor 170 begins executing a Fourier transform. After several seconds or a period equal to the period of the reference signatures, the transformed active signal is stored at the output of the preprocessor 170. Then, array addressing logic 180 begins selecting one reference signature at a time for correlation. Each reference signature is correlated by a correlator 190 with the active signal to determine if the reference signature matches the active signal from the environment.

The comparator 200 compares the magnitude of the output of the correlator 190 with a threshold to determine a match. When searching for events in the active signal such as emergency signals, the correlator 190 is compared with a fixed threshold. In this case, the switch 210 selects a fixed threshold 211 for comparison. If the correlation magnitude exceeds the fixed threshold 211, then the comparator 200 has detected a match. The comparator 200 then activates the correlation identifier register 220 and the correlation magnitude register 230. The magnitude of the comparison result is stored in the correlation magnitude register 230, and the identity of the source is stored in the correlation identifier register 220. For emergency events, an immediate alert signal may be given. This may be an audible signal via a speaker 250, a visual signal via a display 260, a vibration signal via vibrator 270, or some other signal that can be communicated to a user of the SE system 100.

The fixed threshold 211 can be predefined by a programmer or the user of the system 100.

Noise canceling technology is available to improve resolution. Noise canceling microphones or microphone arrays can be used to cancel ambient noise and better detect events. The noise canceling technology can be implemented in software in the detection engine 215, such as in or in association with the preprocessor 170.

Speaker 250 may be a conventional audio speaker or a more sophisticated audio device. For example, a pair of stereo headphones can be used in stead of speaker 250 so that the location of the detected event can be projected by way of the dual stereo channels associated with the stereo headphones. More specifically, assume that two input microphones 130 are employed so that the direction of an event can be determined via different event signal intensities at the two microphones 130. If an emergency signal is detected from the left, then a notification signal could be played on the left stereo channel so that the user knows that the event occurred on the left. This technique can be used within a noisy or sound suppressing vehicle to relay sounds detected by external microphones to internal stereo speakers. Moreover, a map and/or directional arrow can be used in display 260 to present the location or direction of the detected event.

After event detection by the SE system 100, the process is stopped and the array addressing logic 180 is reset. A search for new active signals then resumes.

In some embodiments of the SE system 100, the SE system 100 may be designed to communicate a notification to a remote communications device in order to advise a remote party of detection of an event. Examples include a text message, an email, a voice message, etc.

In a fourth mode of operation, the SE system 100 searches for the best match for the active signal. In this case, the correlation magnitude register 230 is first cleared. Then, the switch 210 selects the output 212 of the correlation magnitude register 230 as the threshold input to the comparator 200. The array addressing logic 180 then sequentially selects all stored references of a set for correlation. After each reference in the set is correlated, the comparator 200 compares the result with previous correlations stored in the correlation magnitude register 230. If the new correlation magnitude is higher, then the new correlation magnitude is loaded into the correlation magnitude register 230, and the respective identifier is loaded into the correlation identifier register 220.

In an alternative embodiment, the correlation process can be performed by an associative process, where the active reference is associated directly with the stored references in a parallel operation that is faster than the sequential operation. New device technologies may enable associative processing. For example, reference memory array 160 can utilize content addressable memory devices for associative processing. ASIC devices and devices, such as the Texas Instruments TNETX3151 Ethernet switch incorporate content addressable memory. U.S. Pat. No. 5,216,541, titled "Optical Associative Identifier with Real Time Joint Transform Correlator," which is incorporated herein by reference, describes optical associative correlation.

In a second alternative embodiment, multiple correlators can be used to simultaneously correlate multiple reference signatures. Each stored reference can have a dedicated correlator or several correlators can each process its own set of stored references. Multiple SE systems 100 can perform correlations with their individual sets of stored references and communicate shared results. Dispersed portable PEDs having the SE systems 100 can sense over a wider geographical range and increase effective processing speed.

This correlation process continues until all stored reference signatures in the set under analysis have been correlated. When the correlation process is completed, the correlation identifier register 220 holds the best match of the identity of the source of the active signal. The identity can be displayed as a photo or text description in display 260 or as a verbal announcement via amplifier 240 and speaker 250. If the final correlation magnitude is lower than a predetermined threshold, then the active signature can be loaded into the reference memory array 160 as a new unknown source.

In a fifth mode of operation, the SE system 100 can attempt to identify unknown sources. Switch 150 is connected to the computer 120 for access to the Internet 110. The computer 120 then searches the Internet 110 for additional references using, for example, a Web browser, associated with the computer 120. The references are downloaded and stored in the reference memory array 160. The unknown source is correlated with the new additional references until a match is found.

The computer 120 can be configured to browse for reference signatures at known World Wide Web (WWW) sites that have such signatures. Furthermore, in accordance with another aspect of the present invention, a server having a database of reference signatures can be constructed and deployed and consulted by the computer 120. Such a configuration is desirable because the format of the reference signatures stored in the server database would be known by the computer 120, making access and analysis of same easy. Moreover, as a novel business method, the user of the system 100 could be charged for access to the reference signatures in the database by the system owner/operator.

Figure 2:
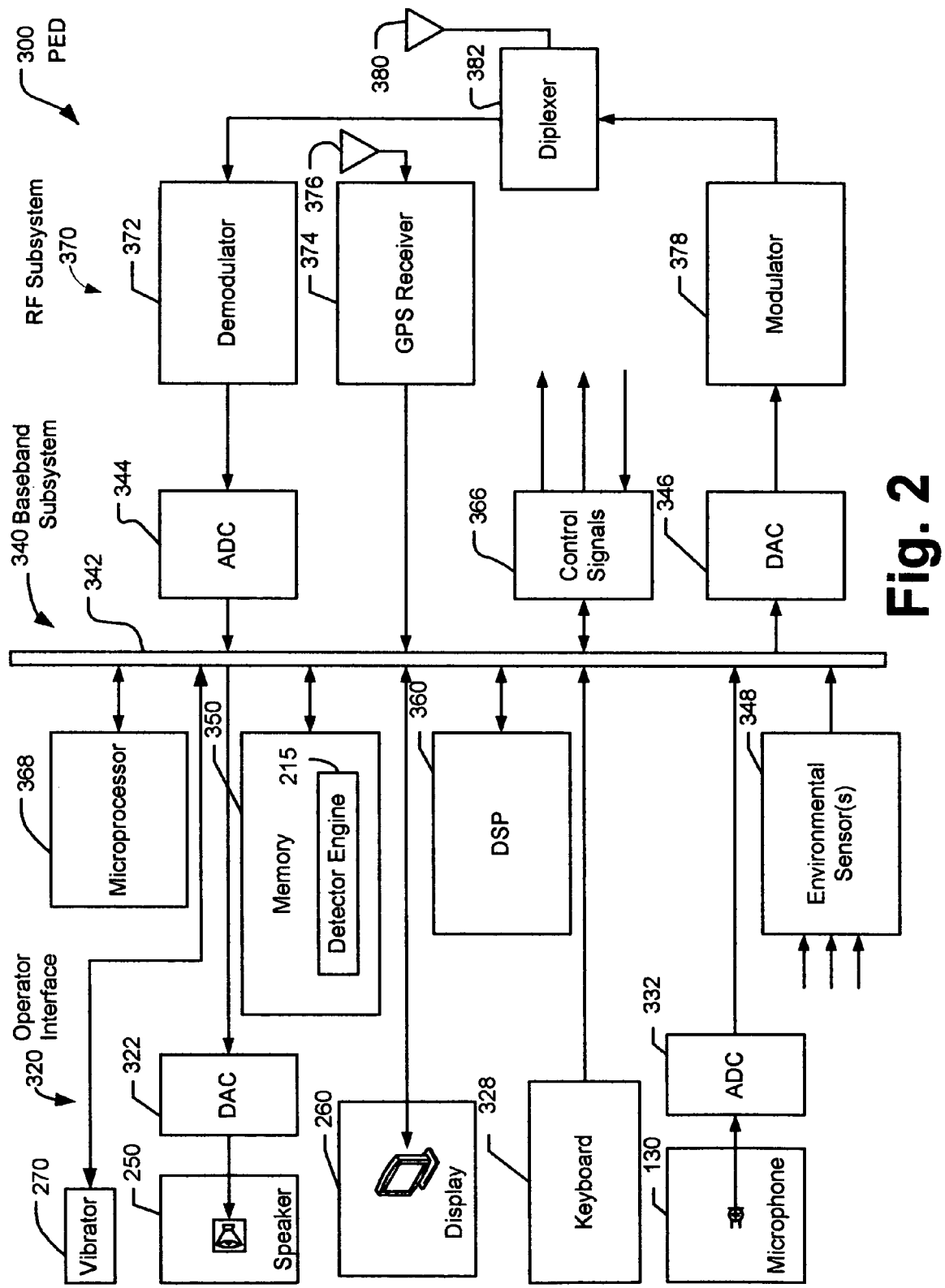
FIG. 2 is a block diagram of an example implementation of a personal electronic device (PED) having the sensory enhancement system of FIG. 1.

FIG. 2 is a block diagram of an example implementation of a portable PED 300 having the SE system 100. The PED 300 can be designed to implement only one electronic based intelligence function, i.e., the SE system 100. However, in the preferred embodiment, the PED 300 is designed with the SE system 100 and at least one other electronic based intelligence function. In general, the PED 300 of the preferred embodiment is implemented by storing suitable SE software (that implements the SE system 100) in a conventional computer-architecture-based PED, such as a wireless (e.g., cellular) telephone or PDA with wireless telephone capability.

A wireless telephone implementation is particularly convenient for acoustic SE, because wireless telephones incorporate a microphone for detection and a speaker for output. Many contemporary wireless telephones incorporate speech recognition software for dialing by voice command. This recognition software can be augmented to provide additional SE capabilities. The speech recognition capability typically includes a learning function whereby the user first enunciates the command while in a special learning mode. This learned command is then stored for later reference, typically with respect to a telephone number. All potential commands are recorded in this manner and stored for reference. Then, in normal operation, when the user enunciates a command, that command is compared with all stored reference commands. The reference that most closely matches the command is used to select and dial the respective phone number.

The acoustic SE system 100 recognizes a much broader set of signals beyond the speech recognized as dial commands. The acoustic SE system 100 stores additional reference signals for recognition. These additional reference signals can be recorded directly by the SE system 100. Or, preferentially, these signals can be obtained as files downloaded from a central repository. Examples include a set of bird songs or a set of registered emergency signals.

Other signals may be computationally derived, such as the Doppler shift of passing vehicles or projectiles. The magnitude of Doppler shift gives the relative speed, and the rate of change of the Doppler shift gives the proximity or closest approach of the vehicle or projectile. Note that only one sensor, or transducer, is needed for determining proximity and speed of an object, whereas the determination of direction would typically require the use of two or more sensors.

Personal Equipment

In architecture, as illustrated in FIG. 2, the PED 300 generally comprises an operator interface 320, a baseband subsystem 340, and an RF subsystem 370.

The operator interface 320 allows the operator to communicate with the baseband subsystem 340. The operator interface 320 incorporates an audio speaker 250, a vibrator 270, a display 260, a keyboard (or dialpad) 328, and an audio microphone 130. The keyboard 328 is used by the operator to generally control the PED 300. Commands or telephone numbers can be entered on the keyboard 328. A display 260 presents the status of the PED 300 to the operator. Speech signals for communications and alert signals for SE are generated digitally in the baseband subsystem 340 and sent to digital-to-analog converter (DAC) 322. The DAC 322 converts digital signals from the baseband subsystem 340 into analog signals to drive the speaker 250. The speaker 250 presents alarm and alert signals as well as received speech signals. Microphone 130 converts acoustic signals into analog input signals for detection by the SE system 100 or for transmission as speech by the PED 300. Analog signals from microphone 130 are converted to digital signals by an ADC 332 for input to the baseband subsystem 340. Speaker 250 and microphone 130 can be stereo devices for the detection and indication of the relative bearing of detected events. Multi-dimensional devices will provide better 3-dimensional position information and improved rejection of ambient noise. Speaker 250 may include a very low frequency mode. A mechanical vibrator 270 can give a mechanical alert signal, if desired.

Baseband subsystem 340 implements control and baseband signal processing functions of the PED 300. For communications functions, the baseband signal processing includes speech recognition, speech compression/decompression, error detection/correction, filtering, and baseband modulation/demodulation. For SE, the baseband signal processing functions include preprocessing, signature array computations, correlation, and detection. Advantageously, when not actively serving for communications, the entire baseband subsystem 340 can be devoted to SE. At least one exception is concurrent emergency signal detection that may be necessary to alert the operator whose attention has been diverted by conversations facilitated by the PED 300.

Baseband subsystem 340 comprises a general purpose microprocessor 368, a memory 350, a digital signal processor (DSP) 360, and other components interconnected by a local interface, which in the preferred embodiment, is a digital communications bus 342. Digital communications bus 342 may be a single bidirectional bus or multiple busses. The operator interface 320 connects directly to the digital communication bus 342. Those skilled in the art will recognize that components of the operator interface 320 and RF subsystem 370 may alternatively be connected to specific interface circuitry that connects to the digital communications bus 342 or that connects to other components, such as the microprocessor 368. An interface alternative is direct memory access (DMA) to transfer data directly into memory 350 or into memory arrays internal to microprocessor 368 or DSP 360.

Examples of dual core processors that can be used in the PED 300 to implement the DSP 360 include, for example, but not limited to, the IBM Power5 multi-chipped processor and the Texas Instruments TMS320C6416 family of digital signal processors. The Texas Instruments TCS1110 chipset is typically used for GSM cell phone handsets. It includes the TBB1110, a dual-core digital baseband processor with both VCP Viterbi decoder and TCP Turbo decoder coprocessors for error correction. Moreover, the Texas Instruments TRF6150 tri-band direct-conversion RF transceiver can implement the RF subsystem 370. GSM is a digital cellular telecommunications system standard as specified in technical specifications such as ETSI TS 101 855.

Microprocessor 368 controls the PED 300 in response to execution of software program instructions stored in memory 350. Software program instructions can be executed directly from memory 350 via bus 342 or batch transferred to memory that is internal to microprocessor 368 or DSP 360 for execution. Microprocessor 368 and DSP 360 may be a single device comprising multiple microprocessors, DSP's and memory devices. DSP devices typically contain multiple functional units including memory, a generalized DSP and multiple specialized pre-programmed DSP's or logic units for implementing features, such as Fourier transformation and Reed Solomon error correction. System-on-a-chip SOC and system-in-a-package SIP technology provide for multiple processors and multiple technologies. Multiple technologies allow for very sensitive environmental detectors and communications receivers as well as high power technology for communications transmitters. Examples include the IBM Power5 multi-chipped processor and the TI C6X family of digital signal processors.

As mentioned, for SE, the baseband signal processing functions include preprocessing, signature array computations, correlation, and detection. These functions can be implemented by the detection engine 215, which in this embodiment, is in the form of software stored in the memory 350 and executed by the microprocessor 368 and/or the DSP 360.

In the preferred embodiment, the microprocessor 368 implements low duty cycle control functions, such as accessing a local list of telephone numbers, call setup, implementation of communications protocols, and general initialization and control of the operator interface 320 and RF subsystem 370. Control commands are transferred from microprocessor 368 to control signals block 366 via bus 342. Control signals block 366 generates signals to the RF subsystem 370 to control frequency synthesis, radiated power, receiver sensitivity, antenna array pointing, initialization, and other communications parameters. Control signals block 366 can be used to pre-program coefficients of multiple input multiple output (MIMO) processors within the RF subsystem 370. Coefficients can be generated at a low duty cycle in the baseband subsystem to offload processing in the RF subsystem 370.

Microprocessor 368 can also access the Internet 110 by wireless connections through the RF subsystem 370. Direct internet access facilitates collection of reference signatures for SE.

DSP 360 performs the complex baseband signal processing operations. These typically involve complex array processing and very high speed arithmetic operations. DSP 360 can also perform the control functions of the microprocessor 368. However, it is generally more economical to utilize the independent microprocessor 368 for control functions.

In addition to the microphone 130, one or more additional environmental sensors 348 (or transducers) may be implemented to monitor the environment and transfer digital replicas of detected events to bus 342 for analysis and action by DSP 360 and microprocessor 368. Sensors 348 may include, for example but not limited to, a microphone, video camera, Hall Effect magnetic field detector, flux gate compass, electromagnetic field detector, accelerometer, barometric pressure sensor, thermometer, ionization detector, smoke detector, gaseous detector, radiation detector, biometric sensor, etc. The set of sensors 348 is optionally provisioned, as needed, to minimize cost. For example accelerometers in the device can warn of impending falls. Web site http://link.abpi.net/1.php?20050822A7 discusses a balance device that utilizes a stereo warning of sway.

The RF subsystem 370 handles signals that are at radio frequencies, which are those that cannot be economically processed by the baseband subsystem 340. Techniques, such as heterodyning, can be used to shift the economical threshold for specific implementations.

In an alternative embodiment, the RF subsystem 370 can be designed to utilize additional frequency bands to detect and access wireless data being transmitted in the environment, for example, signals communicated pursuant to the Bluetooth IEEE 802.15.1 communication protocol, the 802.11 communication protocol etc. External equipment can provide an alert or other information to the system 300.

In the preferred embodiment of the system 300, the system 300 wirelessly accesses the Internet 110 via the RF subsystem 370 for updating an address book, for obtaining updates of software, and for acquiring reference signatures for the SE functions.

In another alternative embodiment, the RF subsystem 370 can be augmented to interrogate radio frequency identification (RFID) tags. As RFID becomes more common, the ability to interrogate and read these devices will become essential and provide significant SE. RFID business cards can be read directly to load the address book of the PED 300, thereby avoiding spelling and transposition errors.

As further illustrated in FIG. 2, a DAC 346 converts digital signals from the bus 342 to analog signals for modulation by a modulator 378. The modulated signals are coupled via a diplexer 382 to an antenna 380. Received signals are coupled from the antenna 380 to the diplexer 382, then to demodulator 372 for demodulation. Analog demodulated signals are converted to digital signals by an ADC 344 and transferred to the bus 342 for final decoding in the baseband subsystem 340. Those skilled in the art will recognize that DAC 346 and ADC 344 can be located at various points within modulator 378 and demodulator 372. As shown, modulation and demodulation are predominantly analog functions, but contemporary designs implement these functions in the digital domain. A significant portion of the modulation and demodulation functions can be implemented in DSP 360 or other DSP elements within the modulator 378 or demodulator 372.

In an alternative embodiment, the antenna 380 may be implemented as a single antenna, multiple antennas, or an antenna array. Diplexer 382 may not be required if independent antennas are used to transmit and receive. Fractal antennas may cover a much wider frequency range allowing operation in multiple frequency bands. Antenna arrays are beneficial for beam forming to enhance signals or to reject interfering signals. Antenna beams offer additional directional information that may be useful in locating the signal source. Display 260 can present a directional arrow indicating the direction to a signal source located by automatic beam steering.

The GPS receiver 374 is another optional element. GPS receiver 374 receives position information from global positioning system satellites via an antenna 376. The position information is transferred directly to the baseband subsystem 340 for processing. The GPS receiver 374 can use the independent antenna 376 or share the common antenna 380. U.S. Pat. No. 6,975,277, titled "Wireless communications device pseudo-fractal antenna," which is incorporated herein by reference, describes an antenna for operating in the GPS and cellular telephone bands, and such antenna can be implemented in the PED 300. Many of the GPS functions, such as coordinate transformation, can be implemented in GPS receiver 374 or DSP 360. Position information from the GPS receiver 374 can be used to alert the operator of proximity to various locations, including those that are hazardous or dangerous. GPS receiver 374 can provide dynamic inputs of speed, direction, and distance traveled to the SE system 100.

Operator Interface

Figure 3:
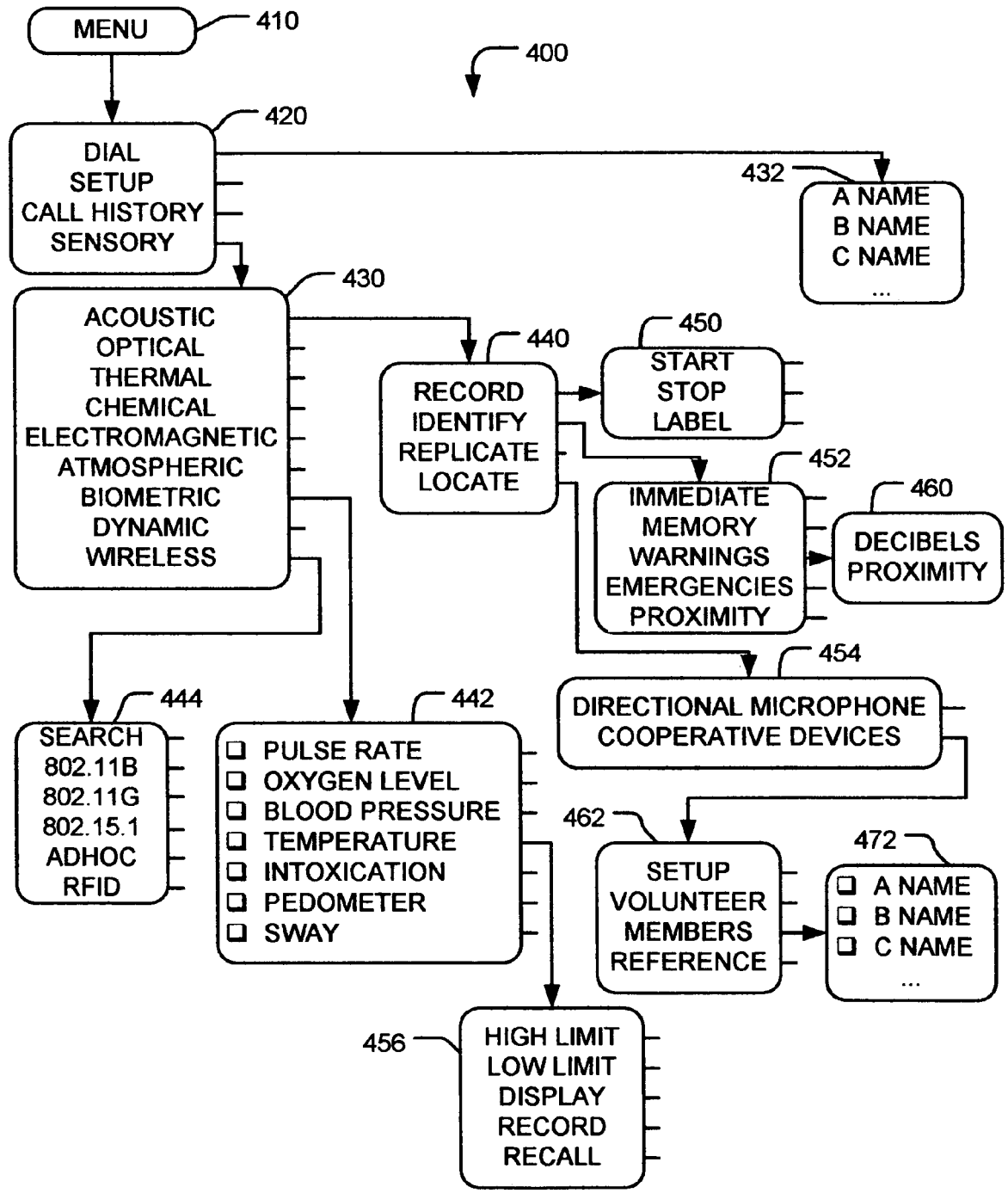
FIG. 3 is a block diagram of an example implementation of a control menu for the PED of FIG. 2.

FIG. 3 illustrates an example of a set of control screen menus 400 that can be used to control the SE system 100 (FIG. 1) associated with the PED 300 (FIG. 2). The screens represent one possible implementation that could be realized in a typical cell phone communications device, such as the commercially available Motorola V60t cell phone. These menus are accessed and displayed through keyboard 328 (FIG. 2) and display 260 (FIG. 2).

The menu access begins by activating the PED 300 and depressing the MENU key 410 or enunciating a voice command into microphone 130 (FIG. 2). This activates a new MENU screen 420 which lists a number of optional commands. To place a conventional phone call, the DIAL command is selected to open the DIAL menu 432. This selection causes display of an alphabetical list of names associated with phone numbers stored in the phone memory 350 (FIG. 2). After selecting the desired name, a call is placed to the respective phone number.

Voice commands are implemented by pressing a voice command key, then enunciating the command, such as "name dial" or "number dial" into microphone 130 (FIG. 2). Speaker 250 (FIG. 2) is then used to issue guidance instructions, such as "say the name". The operator then enunciates the name into microphone 130, the name is repeated via speaker 250, and if confirmed by the operator, then the call is placed. These voice commands can be used to step through the entire control menu 400.

The main menu is accessed by selecting the SENSORY command in the MENU screen 420. This opens the SENSORY screen 430. SENSORY screen 430 allows selection of one or more sensory modes, but preferably multiple sensory modes in this example implementation, that can be active simultaneously. In this implementation, the sensory modes include acoustic, optical, thermal, chemical, electromagnetic, atmospheric, biometric, dynamic, and wireless (corresponding to the types of sensors that are associated with the PED 300). By way of example, a few of these are discussed to clarify the operation of the PED 300.

Selection of the ACOUSTIC command in the SENSORY screen 430 activates the ACOUSTIC screen 440. ACOUSTIC screen 440 may have a large number of choices, only four are shown for exemplary purposes. The RECORD selection of ACOUSTIC screen 440 will activate the RECORD screen 450. This screen enables at least three commands: (1) to start recording an acoustic signature, (2) to stop recording the signature and (3) to label the signature. The label could be typed on keyboard 328 (FIG. 2) or spoken into microphone 130 (FIG. 2). Camera phones can use a photograph of the source for a label. The label is an identifier that can be used by the correlation identifier register 220 of FIG. 1. A number of sub menus (not shown) can be used to enhance recording. The sensitivity of the microphone 130 can be adjusted. An indicator lamp or sound level meter can be displayed in display 260 (FIG. 2) to provide an indication to the operator when an acoustic signal has been detected with suitable quality for recording. The operator can initiate recording when suitable quality is indicated.

A second choice in the ACOUSTIC screen 440 opens the IDENTIFY screen 452. The IDENTIFY screen 452 enables a number of choices for identification of acoustic signals. The IMMEDIATE command initiates a search to identify the audio signals currently detected by the microphone 130. All signatures within reference memory array 160 of FIG. 1 are searched. If a match is found, then the identity of the matching reference will be loaded into correlation identifier register 220 (FIG. 1) and displayed on display 260 (FIG. 2) or announced via speaker 250 (FIG. 2).

The third command in the IDENTIFY screen 452 is for warnings. This opens the acoustic WARNINGS screen 460. Two of several possible warning commands are shown in WARNINGS screen 460. The DECIBELS command will enable a warning if the sound pressure in the vicinity exceeds a safe threshold as measured in decibels. The threshold can be set by the operator. This warning offers protection when the user enters an area of dangerous sound pressure levels. The PROXIMITY command in WARNINGS screen 460 activates the proximity detection system to monitor Doppler shifted acoustic signals and warn of objects passing nearby. Speed and distance are measured and displayed with selectable warning thresholds. The IDENTIFY screen 452 also offers a PROXIMITY command that will issue a warning when the GPS measured position approaches within a selectable range of locations, such as but not limited to, dangerous locations, stored in memory 350.

The LOCATE command of the ACOUSTIC screen 440 activates the LOCATE screen 454, which is used to locate the position of the source of detected acoustic signals. The DIRECTIONAL MICROPHONE command of LOCATE screen 454 will activate directional microphones 130 (two or more are needed to determine direction) that can identify the direction to the source of the acoustic signals by measuring the relative phase of the acoustic wave front as it passes over the device. Optionally, additional microphones 130 can be place at some distance away from the PED 300 to give better resolution of range. These can be wired to the device or communicate via wireless signals, such as those specified in IEEE wireless standard 802.11. This DIRECTIONAL MICROPHONE command can also be used to initialize the sensors. Initialization may require leveling the device and rotating it to align a Hall Effect magnetic compass within the device. The COOPERATIVE DEVICES command of the LOCATE screen 454 is used to coordinate multiple PEDs 300 to determine location. This command opens the COOPERATIVE DEVICES screen 462 which is used to control cooperative operation. The VOLUNTEER command allows the operator to volunteer the PED 300 for cooperative operation with other PEDs 300 in the area. A volunteer signal will be sent to other PEDs 300 identifying the PED 300, its location, and the sensors that are available. The volunteer signal will be sent when first selected and again whenever queried by another PED 300 that is searching for cooperative partners. The MEMBERS command opens the MEMBERS screen 472, which lists the names or phone numbers of nearby devices to be selected as members of the coordination team. The REFERENCE command selects one or more reference signatures that are used to identify the selected environmental event. The reference signatures are transmitted to all of the PEDs 300 participating in the coordination team.

The BIOMETRIC command of SENSORY screen 430 activates the biometric screen 442. The BIOMETRIC screen 442 has check boxes that are selected to activate various biometric monitors for pulse rate, oxygen level, blood pressure, temperature, intoxication, pedometer, and sway. Functions such as the pedometer and sway can be measured directly by internal accelerometers. The GPS receiver 374 (FIG. 2) can be used to calibrate the walking gate automatically or to directly measure the distance traveled. Oxygen level can be measured by folding an appendage sensor of the PED 300 around a finger allowing an internal illuminator and detector to measure blood oxygen levels. The other biometric parameters have corresponding biometric sensors communicatively coupled to the PED 300 by physical wires or wireless signals. Selection of any biometric parameters in BIOMETRIC screen 442 will open the MONITOR screen 456 where independent thresholds can be set for warnings on each parameter. The parameter values can be continuously displayed on display 260 or announced on speaker 250. Audio announcements can be issued when values change, when limits are exceeded or periodically. A running chronological record of the parameters can be maintained in memory 350 (FIG. 2). Parameters can be recorded in files with respect to a real time reference derived from GPS receiver 374. Recorded parameter files can be recalled later for display as a graph on display 260 or communicated to a central repository or other device by physical wires or wireless signals.

The WIRELESS command of SENSORY screen 430 activates the WIRELESS screen 444. The SEARCH command of WIRELESS screen 444 initiates a search for wireless signals. Wireless signals may be long range, such as weather warnings. Others may be issued by nearby equipment. Dangerous heavy equipment can be modified to generate wireless signals, such as for example but not limited to, those specified in IEEE wireless standard 802.11b or 802.11g. These signals can warn of the nearby equipment and issue detailed instructions to be followed when in close proximity to the equipment.

A wireless signal could be used to warn against cell phone use and shut down the cell phone after an adequate warning period for the conversation to be politely terminated. U.S. Pat. No. 6,943,667, which is incorporated herein by reference, describes a method for waking a device in response to wireless network activity and presents a method for determining if a wireless signal is from a known source. The foregoing methods can be implemented in the PED 300 so that the PED 300 can detect and identify wireless network activity. Furthermore, U.S. Pat. No. 6,222,458, which is incorporated herein by reference, describes an automatic cell phone detection system/method at a combustible delivery station that provides for turning off a pump when a cell phone is detected. Such a system/method can be implemented in the PED 300 so that the PED 300 can turn off its corresponding transmitter when in close proximity to a combustible or explosive environment. The CHEMICAL command of SENSORY screen 430 can be used to detect combustible, explosive, or toxic environments as well as combustion products of smoke and carbon monoxide.

The menu screens preferably include redundancy, allowing the user to activate specific detectors from several different screens to fit the preferences of the user. The ATMOSPHERIC command of SENSORY screen 430 can be used to detect a range of atmospheric conditions including but not limited to temperature, barometric pressure, humidity, precipitation, lightning, tornadoes, wind speed, wind direction, dew point, fog, smoke, gaseous vapors, airborne particulates, airborne pathogens, sound pressure, solar intensity, radiation, etc. A different set of these parameters can be selected by the user for outdoor activity or in confined, possibly contaminated areas. U.S. Pat. No. 6,232,882, titled "Warning System and Method for Detection of Tornadoes," which is incorporated herein by reference, describes a system and method for detecting and differentiating between lightning strikes and tornado generated electromagnetic signals. Such system and method can be implemented in the PED 300 of the present invention.

Spectrogram Example

Figure 4:
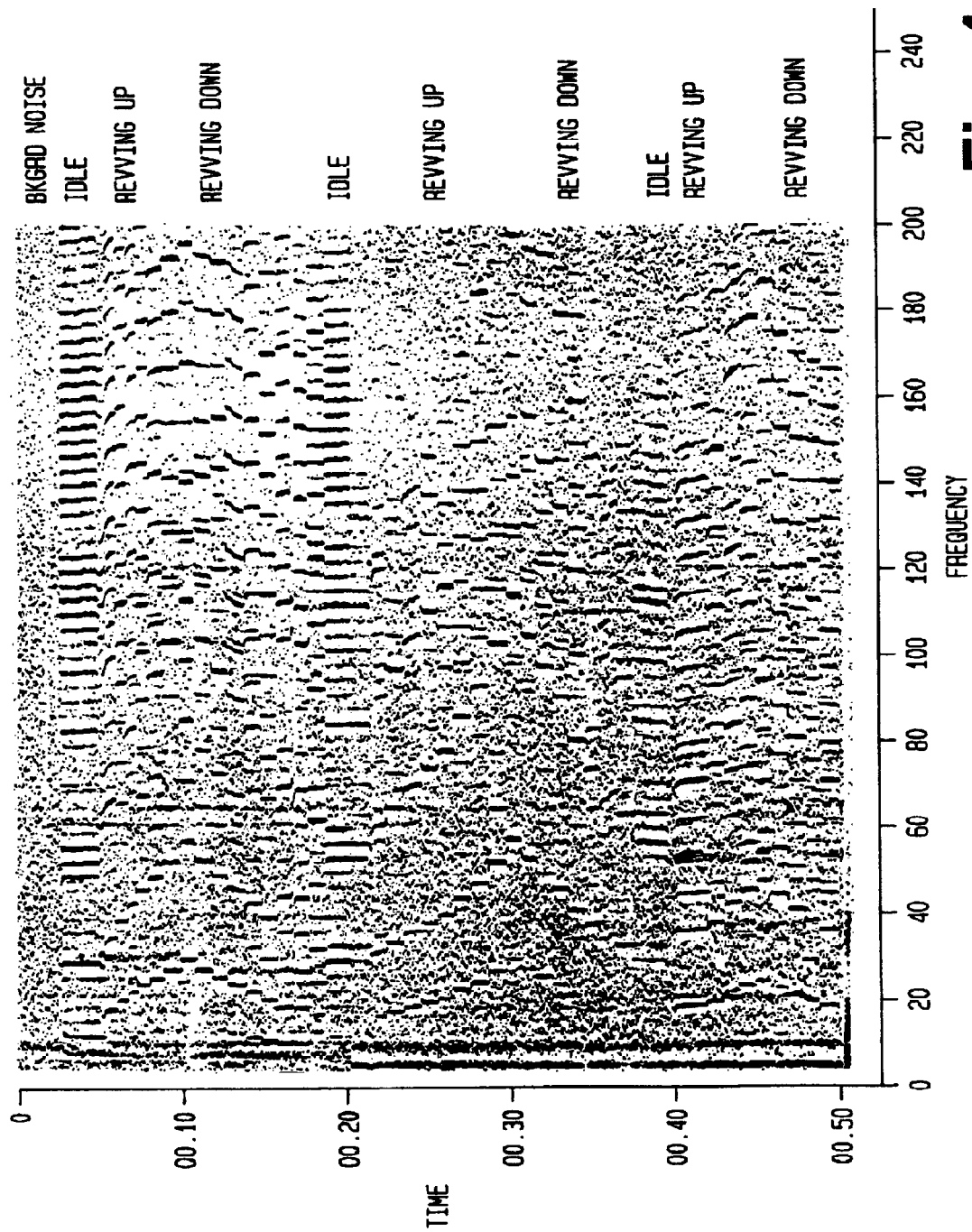
FIG. 4 is an example spectrogram graph illustrating measurement of acoustic data in three dimensions (time, frequency and magnitude) that can be analyzed in order to detect an acoustic event.

FIG. 4 is one nonlimiting example of a spectrogram as may be presented in a printed document. In this example, the abscissa x-axis is frequency in Hertz (Hz) and the ordinate y-axis is time in seconds. This plane of the graph depicts changes in frequency with respect to time. Any acoustic source will generate multiple frequencies and all are shown in the spectrogram. A third dimension, the magnitude of each frequency is displayed by variations in the intensity or darkness of each plotted point. For calculations and correlation, this same information is stored in reference memory array 160 as a three dimensional array representing time, frequency, and magnitude.

U.S. Pat. No. 6,173,074, titled "Acoustic Signature Recognition and Identification," which is incorporated herein by reference, describes a system and process for performing such calculations and correlation that can be implemented in the SE system 100. In essence, the system and process use a Fast Fourier Transform (FFT) to compute the spectrogram image of frequency versus time, which is then used to identify machinery.

Doppler Calculations

Figure 5:
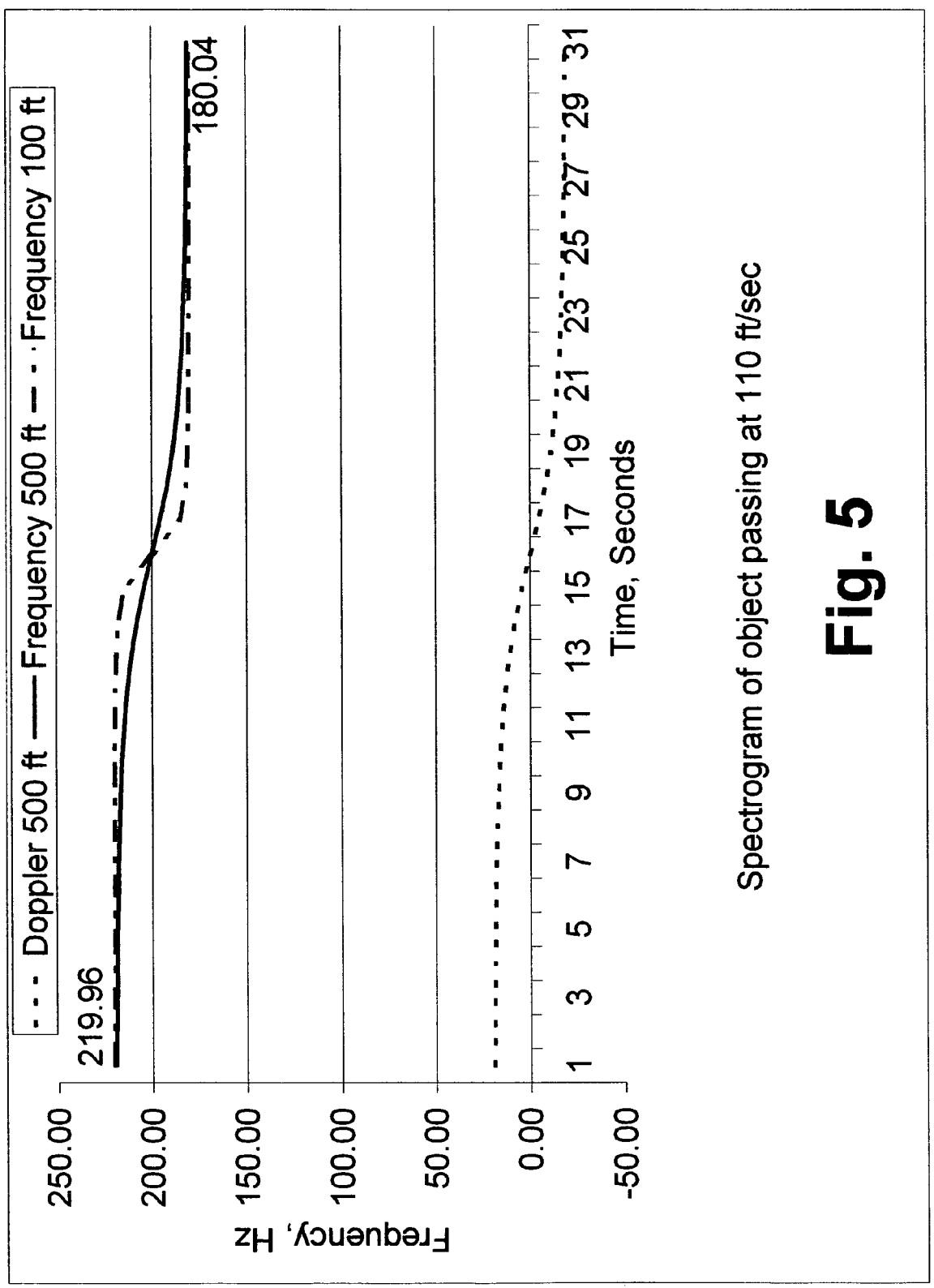
FIG. 5 is an example spectrogram graph illustrating Doppler calculations in connection with measured acoustic data.

Doppler frequency calculations are well known in the art. Doppler frequency shift of acoustic or electromagnetic waves occurs when the source of a signal is in motion with respect to the observer. The frequencies of signals emanating from an approaching object are shifted up to higher frequency in direct proportion to the relative speed. When the object passes its point of closest approach and begins to recede, then the signal will be shifted to lower frequency as shown in FIG. 5. The frequency at the point of closest approach is the true frequency of the signal. This true frequency, $f_t$, can be computed as the average between the original approach frequency, $f_a$, and final departure frequency, $f_r$. One half of the difference between the original approach frequency and final departure frequency indicates the Doppler frequency shift, $f_d$, which is used to estimate the speed of the object, $s_a$, from the known propagation speed of the wave, $s_p$.

$$f_t = (f_a + f_r)/2$$

$$f_d = (f_a - f_r)/2$$

$$s_a = s_p * f_d / f_t$$

FIG. 5 is an example spectrogram of an object traveling at 110 ft/s and passing at two different ranges of 500 ft and 100 ft. For this example, the audio noise emanating from the object is 200 Hz corresponding to reciprocating equipment running at 12,000 rotations per minute (rpm). For illustrative purposes, the actual Doppler frequency shift is derived from the spectrogram for passage at 500 ft and plotted at the bottom of FIG. 5. The equations above yield an estimated true frequency of 200 Hz, an estimated Doppler frequency shift of 19.96 Hz, and an estimated speed of 109.8 ft/s. If a known frequency is emanating from the object, then the Doppler shift and speed can be computed on first approach. If the frequency is unknown, then it is best to wait for departure and estimate the true frequency as outlined above using the broadest possible frequency spread. The Doppler frequency shift and corresponding range can be underestimated for objects that pass far away.

The rate of change in frequency indicates the distance of closest approach, D. The apparent frequency will change as a sinusoidal function of the bearing to the passing object. The bearing B relative to a zero degree angle at closest approach can be computed as a function of this apparent frequency f.

$$B = \arcsin((f - f_t)/f_d)$$

The rate of change is computed by measuring the time T required for a predetermined frequency shift. Distance run $D_r$ is then computed from the estimated speed $s_a$ to be $D_r = T * s_a$. Knowledge of the distance run and the bearing between two points establishes a triangle and enables calculation of the distance of closest approach. A number of solutions are available, but one of the simplest is to time the passage in a 60 degree cone from +30 degrees to −30 degrees where the frequency will change from $f_t + f_d/2$ to $f_t - f_d/2$. Within this 60 degree cone, the target is in close proximity for the final measurement and the distance of closest approach is $D = D_r/(2*\tan(B))$, where B=30 degrees. This calculation can be used for any symmetric measurements across the point of closest approach.

In general, a closed solution can be computed from any two points. Computational accuracy improves at close range where the bearing is less than 45 degrees. At times $T_1$ and $T_2$, respective frequencies of $f_1$ and $f_2$ are measured. The time of transit between the two points is $T = T_2 - T_1$, the distance run between these two points is $D_r = T * s_a$, and the distance of closest approach is computed from the bearings to each point $B_1$ and $B_2$ to yield $$D = D_r \cos(B_1) \cos(B_2) / \sin(B_1 - B_2)$$

Figure 6:
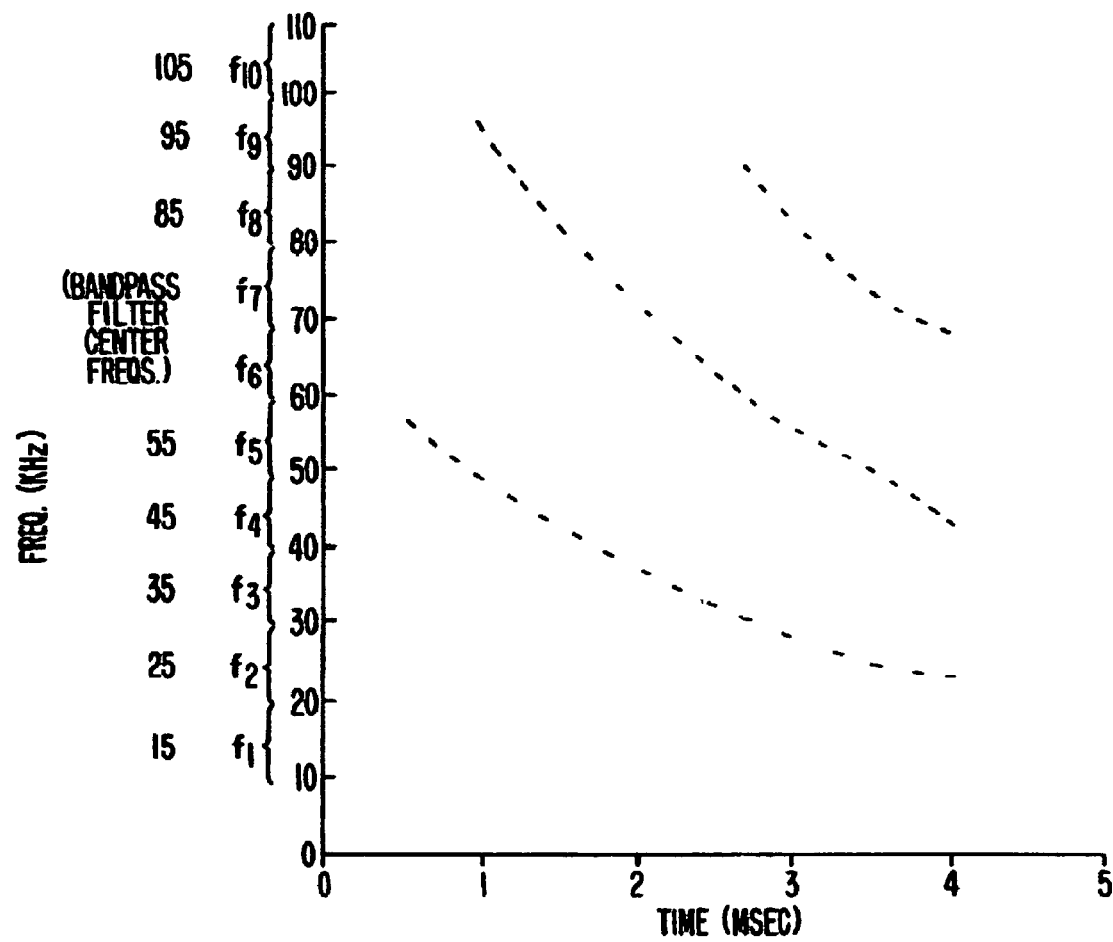
FIG. 6 is an example spectrogram graph constructed by zero crossing analysis of sub-bands.

Most objects generate a packet of multiple frequencies. The centroid of the packet can be used to simplify the calculations. U.S. Pat. No. 6,853,695, titled "System and Method for Deriving Symbol Timing," which is incorporated herein by reference, describes a centroid calculation process for timing estimates that can be used for a packet of frequencies. The foregoing process can be implemented in the SE system 100. U.S. Pat. No. 4,640,134, titled "Apparatus and Method for Analyzing Acoustical Signals," which is incorporated herein by reference, describes a process for zero crossing analysis of sub-bands to construct acoustical spectrograms, as shown in FIG. 6. The aforementioned process can also be implemented in the SE system 100.

Magnitude or intensity of the sound waves can be expected to increase on approach and decrease on departure. But, magnitude or the volume of sound can vary for many reasons and may not be sufficiently reliable for range estimates when used alone. However, a steady increase in sound power magnitude with no change in frequency indicates a potential collision.

A second method for computing range is the use of comb filters to detect only Doppler shifted frequencies. This method is used, for example, in Doppler weather radar, which detects moving weather phenomena. It relies on knowledge of the frequency of the original signal which is transmitted locally, reflects off of the target and returns with Doppler shifted frequency proportional to the speed of the target.

Another method for calculating the range to moving objects is to compute the range from differences in the relative speed of propagation of different signals. It is well known that the 186,300 miles per second speed of light is much faster than the 1100 ft/s speed of sound in air. Many people estimate the distance to dangerous lightning storms by counting the seconds between the flash of lightning and the arrival of the sound of thunder. For most purposes, the speed of light is instantaneous so that each second of delay equates to 1100 feet distance from the lightning strike. An SE system 100 with optical and audio capability can use this same or a similar method to estimate distance. The RF subsystem 370 can detect radio frequency signals generated by the electrostatic discharge of lightning when indoors or beyond the visual range of the lightning. For greater accuracy, air pressure and temperature can be measured to accurately predict the local speed of sound.

A differential acoustic method can be applied to moving vehicles. An acoustic sensor can be placed in the ground or water near the SE system 100. The speed of sound in water is 4856 ft/s. Acoustic waves propagating through the ground or water will be detected earlier than acoustic waves propagating through the air. The difference in propagation speed can be used to compute the range to the object directly. This technique can be implemented in the canes used by visually impaired individuals. An acoustic sensor in the tip of the cane will detect approaching objects before an acoustic sensor placed higher up to monitor air borne acoustic signals. The difference in time of arrival at the two sensors can be used to compute range.

Sound Power Level Warnings

The National Institute of Health (www.nih.gov) and National Institute for Occupational Safety and Health (http://www.cdc.gov/niosh/98-126.html) recommend no more than 15 minutes of exposure to high sound power levels above 100 dBA and no more than 8 hours of exposure above 85 dBA. The SE system 100 can be designed to give an immediate warning of high sound pressure levels or give a weighted measure over time so that the 100 dBA warning will be given after 15 minutes of exposure. Cumulative exposure can be accurately computed by the SE system 100 for all sound level exposure throughout the day. For each 3 dB increase in sound power level above 85 dBA the recommended exposure time limit is cut in half. For a sound power level of $P_i$ in dBA the maximum exposure time is $$T_i = 8/\log_{10}^{-1}((P_i - 85)/10) \text{ hours}$$

or $$T_i = 8/\text{antilog}_{10}((P_i - 85)/10) \text{ hours}.$$

The SE system 100 measures the cumulative exposure at all levels above 85 dBA by recording the total time $t_i$ that the sound power level is in each range $P_i$. Then, the cumulative exposure dose D relative to a maximum exposure limit of 100% is given by $$D = (t_1/T_1 + t_2/T_2 + \ldots + t_n/T_n) * 100\%.$$

Audio devices that use ear plugs or ear phones could be modified to implement the SE system 100 in order to provide a back pressure measurement such that the device can compute the sound pressure within the ear. Alternatively, the ear plug sound power level can be calibrated with respect to the volume setting on the audio device so that the sound power level can be computed from the volume setting. This calculation can be used to alert the operator of dangerous volume levels. For safety, the device could automatically reduce volume levels to maintain safe sound levels.

Physical Conditioning Assistance

The sensors associated with the SE system 100 can be used to assist athletes in physical conditioning. A pulse rate monitor can alert when the pulse rate has achieved the desired level and warn of excess exertion or irregular pulse rate. For example the PED 300 can be strapped to the arm of the athlete where the SE system 100 pressure sensor or microphone can sense the pulse rate. Performance measures can be augmented by measurement of the blood oxygen level, hydration and other physiological parameters. Ambient air monitoring by the SE system 100 can warn of dangerous pollution in the local environment where over excursion may be dangerous. The GPS receiver 374 (FIG. 2) in each PED 300 yields position information that can give the athlete real time speed and distance run in the field. Casual conditioning attributed to walking and other motion throughout the day can be recorded by the PED 300. The PED 300 can provide audio entertainment, music or exercise instructions while exercising. A brief audio announcement by the PED 300 can serve to periodically alert the athlete to progress or dangerous conditions.

Near Field Communications

The RF subsystem 370 can include a near field communications (NFC) wireless transceiver. This enables the user to communicate with a station by holding the PED 300 within four inches of the station. This method is commonly used to make purchases similar to credit card transactions by simply holding the device near a point of sale reader. As a result, the PED 300 can be used to make point of sale transactions. This secure technology can also be used by the PED 300 to exchange confidential information such as medical records, reference signatures, biometric parameter monitoring instructions and recorded results.

Personal Tracking Tags

The RF subsystem 370 can be augmented to interrogate tracking tags, such as radio frequency identification (RFID) tags or other transponders. The tag can be placed on a child or in a briefcase, portable computer, purse, or any other item that may become lost, forgotten, or stolen. The tag will be queried periodically by the SE system 100 in the PED 300 to determine that the tag is in close proximity. If the tag is not in close proximity, then an alarm can be issued by the output devices 225 of the PED 300. Signal power and time delay between query and response will give an indication of range. Automatic beam steering antenna arrays can provide a directional indication to the lost item. At some frequencies multi-path reflections of the signal may degrade the directional information.

The tag should be a bracelet or other interlocking mechanism that has a positive indication of attachment. The bracelet can be placed on a child's arm, briefcase handle or purse strap. Removal of the bracelet should cause an immediate alarm. The tracking tag can be a label that can be placed on any item to be tracked. The label can be inconspicuously placed to deter removal. Alternatively, the tag can be placed where its removal would be immediately obvious to other individuals, such as in a child's shoe.

The tracking tag can issue an alarm in response to additional environmental information such as excessive heat or humidity in the vicinity of the tracked item. For example if a child should fall into a swimming pool even the simplest tracking tag should fail to respond resulting in an immediate alarm. Transponder tracking tags of higher complexity can incorporate their own SE system 100 that communicates selected environmental information back to the PED 300.

Chemical Detectors/Transducers

The SE system 100 can be designed to detect chemical changes in the environment. A portable PED 300 having the SE system 100 that can detect dangerous chemical changes, such as smoke, would be beneficial. In this configuration, the PED 300 is essentially a mobile smoke and carbon monoxide alarm.

The SE system 100 can be designed to detect potential impairment of an operator's senses by judgment of motion and dexterity in operation of the PED 300.

One or more chemical sensors can be utilized to detect intoxication as demonstrated by pending U.S. Patent Application No. 20040081582, titled "Cell Phone/Breath Analyzer," filed Apr. 29, 2004, which is incorporated herein by reference.

One or more chemical sensors for continuous monitoring for toxic fumes can also be implemented in the SE system 100. CO and NO can be detected by the system and process described in pending U.S. Patent Application No. 20040016104, titled "Electrodes for Solid State Gas Sensor," filed Jan. 29, 2004, which is incorporated herein by reference. U.S. Pat. No. 6,638,407, titled "Electrochemical Gas Sensor with Gas Communication Means," which is incorporated herein by reference, describes a detector that can be used to detect CO. Such detectors could be included in the SE system 100 for continuous protection.

U.S. Pat. No. 6,830,668, titled "Small Volume Electrochemical Sensor," which is incorporated herein by reference, describes a sensor that can be implemented in the SE system 100 for the purposed of conducting field analysis of liquid samples.

Cooperative Operation of Multiple PEDs

Two or more PEDs 300 can function cooperatively to provide sensory enhancement over a wider range than that covered by a single PED 300. Multiple cooperating PEDs 300 can simultaneously monitor for selected environmental events as illustrated in FIG. 7.

COOPERATIVE DEVICES screen 462 (FIG. 3) is used to coordinate two or more PEDs 300. The VOLUNTEER command allows the operator to volunteer the PED 300 for cooperative operation with other PEDs 300 in the area. A volunteer signal will be sent to other PEDs 300 identifying the PED 300, its location, and the sensors that are available. The volunteer signal is sent when first selected and again whenever queried by another PED 300 that is searching for cooperative partners. The MEMBERS command opens the MEMBERS screen 472, which lists the names or phone numbers of PED 300 devices to be selected as members of the coordination team. The REFERENCE command selects one or more reference signatures that are used to identify the selected environmental event. The reference signatures are transmitted to all of the PEDs 300 participating in the coordination team. The PEDs 300 should be dispersed across the area of interest to cover the widest possible range. The locations of the PEDs 300 can be predetermined or they can travel randomly. Each of the PEDs 300 then commences simultaneous monitoring for the selected event.

Figure 7:
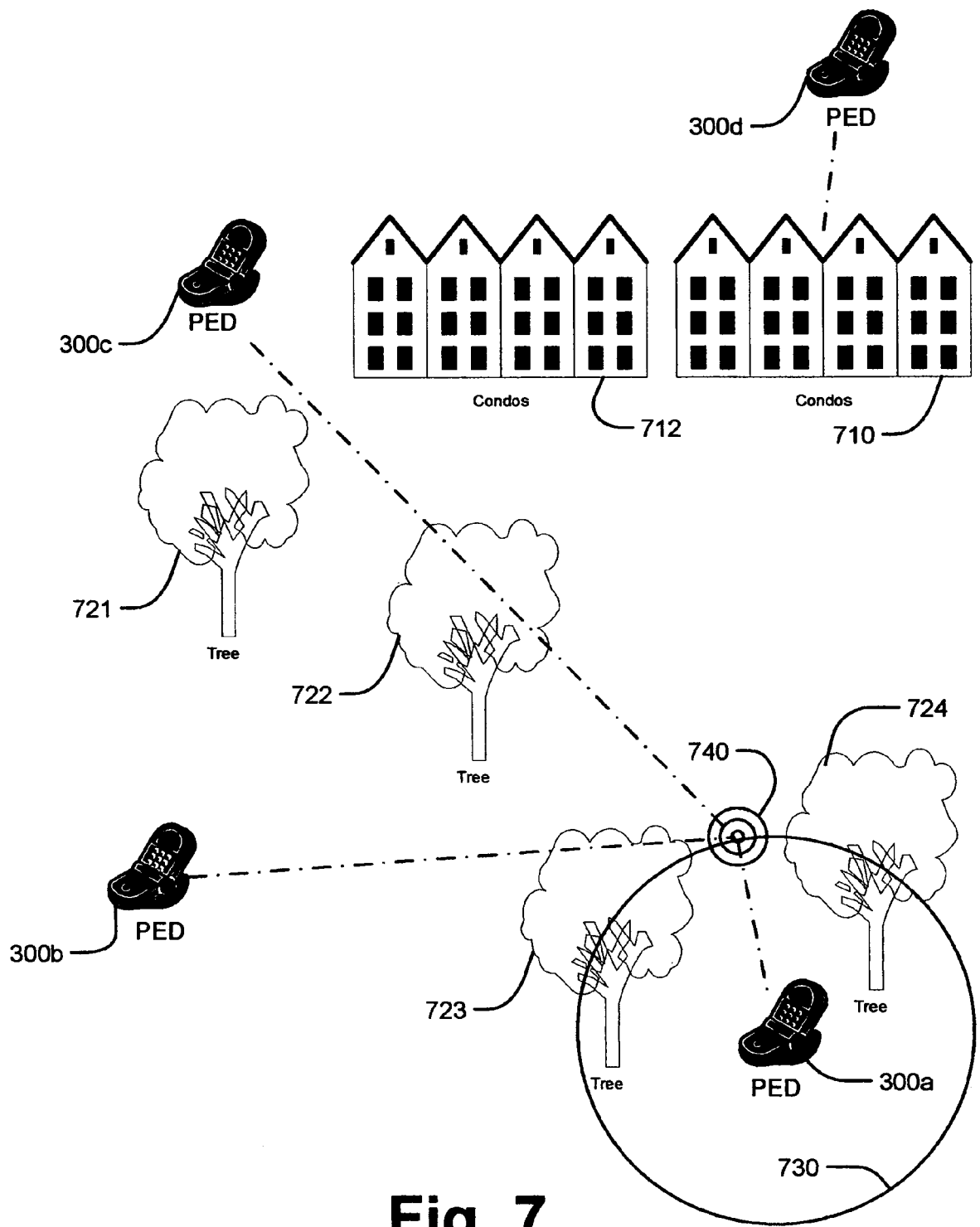
FIG. 7 is a diagram illustrating cooperative operation of multiple PEDs.

As illustrated in FIG. 7, events occurring at target location 740 are easily detected within range circle 730 of nearby cooperating PED 300a. Cooperating PED 300a can communicate the detected events to other cooperating PEDs. In some cases the only position information is the location of the single detecting cooperating PED 300a and possibly the range from the detecting cooperating PED 300a. In other cases multiple cooperating PEDs 300a, 300b and 300c may detect the event and triangulation between the multiple cooperating PEDs 300a, 300b and 300c can determine the target location 740 with greater accuracy. Some cooperating PED devices, such as cooperating PED 300d may be blocked from detecting the event by range, terrain or buildings such as condos 710 and 712. Beneficially, all of the cooperating PEDs can be notified of the detected event by wireless signals communicated from the detecting PED or PEDs.

Upon detection of the selected event in one or more PEDs 300, the GPS receiver 374 (FIG. 2) in the detecting PED 300 can accurately identify the location and time of detection at the detecting PED 300. The position and time of detection at each detecting PED 300 can be communicated to all participating PEDs 300 by wireless signals, such as Bluetooth, IEEE 802.11 or ordinary text messaging between cell phones. Correlation of three or more detecting PEDs 300 will allow an accurate position determination of the source of the event. If the source is moving, then the direction of travel can be determined by computing the vector between successive positions. Each PED 300 can calculate and display the location of the event. This process can be used to locate the source and motion of any signals such as a toxic cloud, alarm signal, wireless signal, weapons discharge, lightning strike, tornado, or person talking. A team of individuals can locate a missing person or child by coordinating their PEDs 300 in a search for the voice print of the missing person or child. U.S. Pat. No. 6,232,882, titled "Warning System and Method for Detection of Tornadoes," which is incorporated herein by reference, describes a method for detecting, differentiating, and locating lightning strikes and tornado generated electromagnetic signals. U.S. Pat. No. 6,944,466, titled "Mobile Location Estimation in a Wireless Communication System," which is incorporated herein by reference, describes a method for locating the source of a wireless signal based on signals received at multiple receiver stations. Such systems/methods can be implemented in the portable cooperating PEDs 300.

Other Examples of Applications

The present invention has many applications, a few non-limiting examples of which have been described. A few more are set out hereafter.

The SE system 100 can be incorporated in a wireless telephone to monitor its microphone for emergency warnings, such as the siren of an emergency vehicle, bell of a railroad crossing, drawbridge bell, etc. Upon detection of an emergency signal, the telephone can be designed to immediately cease its current operation and give an immediate unmistakable audible warning. If equipped with a display device, the telephone can also produce a visual alert. If equipped with a mechanical vibrator, the telephone can produce a vibration alert through one of its normal ring signaling modes.

The SE system 100 can be used for detecting a siren or alert signal from a smoke detector. Conventional smoke detectors suffer from common failures, such as a run down battery. Weak siren signals or low battery signals can be detected by the PED 300 and the user can be alerted with a visual, audio, and/or mechanical queue. The SE system 100 can provide redundancy by directly detecting smoke, carbon monoxide or other toxic vapors. The portable PED 300 with SE system 100 is used frequently; assuring that a weak battery or degraded power will be quickly detected and corrected.

The SE system 100 can be designed to detect bird songs. Naturalists may wish to better hear or identify sounds of nature, such as bird songs. The PED 300 can be designed to store reference signatures of bird songs, to detect bird songs, and to alert the user of such detection. The identity of the bird can be displayed and, in some implementations, the direction can be indicated via an arrow on the display or via an audible indication. A PED 300 with mapping GPS navigator capability can superimpose the directional vector on the GPS map display.

The SE system 100 can be used for monitoring biometric sensors. Conventional biometric heart or respiratory monitors may be inconvenient. By implementing these features in the PED 300, the features will be always available. Low battery conditions will be immediately apparent.

The SE system 100 can be designed to sense temperature and monitor it in connection with a threshold. As an example, a temperature warning system can be implemented. A user can be alerted when the environmental temperature exceeds a predefined threshold.

The SE system 100 can be designed to monitor for wireless signals, such as IEEE 802.15.1, 802.11, or other wireless communications protocols. Equipment in the environment could be designed to transmit a signal to indicate any abnormal condition in the nearby equipment, and the SE system 100 can detect the abnormal condition and advise the user of same.

The SE system 100 can be designed to identify individuals participating in nearby conversations. Individuals can be detected by voice print analysis. This could be useful in detecting terrorist suspects.

The SE system 100 can be designed to detect the discharge of a firearm. Law enforcement officers may wish to locate the source of sounds, such as weapons discharge.

The SE system 100 can be designed to assist in military applications. For example, military applications may require the rapid detection of the sonic report of a passing projectile which may arrive seconds before the report of the weapon that discharged the projectile.

U.S. Pat. No. 5,703,321, which is incorporated herein by reference, describes a device for locating artillery and sniper positions. It basically describes a pyrotechnic device which is deployed in large numbers to signal when the acoustic signature of a munitions discharge is detected in the immediate vicinity. The PED 300 can be designed to provide the same or similar functionality. Multiple cooperating PEDs 300 in audible range of the discharge can record the time of detection at each PED 300. The GPS receiver 374 (FIG. 2) in each PED 300 can accurately identify the time of arrival of the wave front at the known GPS position of the PED 300. The time of arrival and position at each PED 300 can be communicated to the others by wireless signals, such as the ordinary text messaging used in cell phones. Correlation of three or more PEDs 300 will allow an accurate position determination of the source of the discharge. Each PED 300 can calculate and display the position of the discharge. This same process can be used to locate the source of any acoustic signals such as an alarm signal or person talking.

U.S. Pat. No. 5,703,835, which is incorporated herein by reference, describes a system for effective control of urban environment security. It describes an urban security gun shot detection system that uses sensors mounted in fixed positions throughout the urban area. The PED 300 can be designed to implement the same or a similar technique. The PEDs 300 could be the radios carried by law enforcement personnel or could be cell phones associated with citizen volunteers. The GPS receiver 374 (FIG. 2) in each PED 300 provides the position of mobile PEDs 300 allowing accurate triangulation to determine the location of the gun shot.

The SE system 100 can be designed to detect emergency sirens or approaching vehicles. Those with hearing impairments would benefit by a visual or vibration alert to dangerous situations, such as emergency signals or approaching vehicles.

The SE system 100 can be designed to include a GPS receiver 374 (FIG. 2). In one embodiment, among others, the SE system 100 can detect and provide an alert when the PED 300 is within a certain region of the earth or at a particular location.

The SE system 100 can be designed with an accelerometer that warns of impending falls. See web site http://link.abpi.net/l.php?20050822A7 that discusses a balance device that utilizes a stereo warning of sway.

Variations and Modifications

In concluding the detailed description, it should be noted that the terminology "preferred embodiment" herein means the one embodiment currently believed by the inventor(s) to be the best embodiment of a plurality of possible embodiments. Moreover, it will be obvious to those skilled in the art that many variations and modifications may be made to the preferred embodiment(s) without substantially departing from the principles of the present invention. All such variations and modifications are intended to be included herein within the teachings of the present invention in this document and to be protected by the scope of the following claims.

At least the following inventions are claimed:

1. A personal electronic device (PED) that can be transported with a user, comprising:
   first means for performing a first electronic based intelligence function; and
   second means for performing a second electronic based intelligence function, the second means comprising:
      a transducer;
      means for detecting an event in an environment to which the PED is exposed via the transducer; wherein the detecting means further comprises:
         means for storing a plurality of reference signatures having frequency domain characteristics;
         means for preprocessing a sensed signal by converting the sensed signal to a frequency domain signature; and
         means for determining when the sensed signal corresponds with one of the reference signatures by correlating the frequency domain signature with the plurality of reference signatures and
      means for producing a notification upon detection of the event.

2. The PED of claim 1, further comprising:
   means for receiving an analog sensed signal; and
   means for translating the analog sensed signal to one of the reference signatures via fast Fourier transform.

3. A personal electronic device (PED) that can be transported with a user, comprising:
   first means for performing a first electronic based intelligence function; and
   second means for performing a second electronic based intelligence function, the second means comprising:
      a transducer;
      means for detecting an event in an environment to which the PED is exposed via the transducer; and
      means for producing a notification upon detection of the event;

wherein the event is a moving object in motion and wherein the second means further comprises:
    means for determining a Doppler shift associated with the moving object; and
    means for determining a proximity and speed of the moving object based upon the Doppler shift.

4. A personal electronic device (PED) that can be transported with a user, comprising:
    first means for performing a first electronic based intelligence function; and
    second means for performing a second electronic based intelligence function, the second means comprising:
        at least two transducers;
        means for detecting an event in an environment to which the PED is exposed via the transducers; and
        means for producing a notification upon detection of the event; and
        means for determining a direction associated with the event based upon signals sensed by the at least two transducers.

5. A personal electronic device (PED) that can be transported with a user, comprising:
    first means for performing a first electronic based intelligence function; and
    second means for performing a second electronic based intelligence function, the second means comprising:
        a transducer;
        means for detecting an event in an environment to which the PED is exposed via the transducer; and
        means for producing a notification upon detection of the event; and
        means for defining a range around the PED, inside of which the event may be detected and outside of which the event cannot be detected.

6. A personal electronic device (PED) that can be transported with a user, comprising:
    means for storing identification information relating to a plurality of events; and
    means for enabling the user to select an event from the stored identification information relating to the plurality of events;
    means for storing reference signatures;
    means for detecting the event in an environment associated with the PED, the detecting means comprising:
        means for sensing a signal in the environment;
        means for correlating the signal with one of the reference signatures; and
        means for indicting the detecting of the event based upon the correlating; and
    means for producing a notification upon the detecting of the event.

7. A personal electronic device (PED) that can be transported with a user, comprising:
    means for storing a reference signature;
    means for detecting an event in an environment associated with the PED comprising:
        means for sensing a signal in the environment;
        means for correlating the signal with the reference signature; and
        means for indicting the detecting of the event based upon the correlating; and
    means for producing a notification upon the detecting of the event;
    wherein the PED has a computer based architecture and further comprising:
    a keyboard;
    a display; and
    user interface software that enables the user of the PED to interact with the PED using the keyboard and the display, the user interface software enabling the user to store the reference signature and enabling the user to associate a picture with the reference signature.

8. A personal electronic device (PED) that can be transported with a user, comprising:
    means for storing a reference signature;
    means for detecting an event in an environment associated with the PED comprising:
        means for sensing a signal in the environment;
        means for correlating the signal with the reference signature;
        means for indicting the detecting of the event based upon the correlating; and
    means for producing a notification upon the detecting of the event;
    wherein the PED has a computer based architecture and further comprising:
    one or more transducers for measuring environmental characteristics;
    a keyboard;
    a display; and
    user interface software that enables the user of the PED to select which of the one or more transducers are to be operational by providing one or more inputs via the keyboard and receiving one or more outputs via the display.

9. A personal electronic device (PED) that can be transported with a user, comprising:
    means for storing a reference signature;
    means for detecting an event in an environment associated with the PED comprising:
        means for sensing a signal in the environment;
        means for correlating the signal with the reference signature;
        means for indicting the detecting of the event based upon the correlating; and
    means for producing a notification upon the detecting of the event;
    wherein the PED has a computer based architecture and further comprising:
    a keyboard;
    a display; and
    user interface software that enables the user of the PED to interact with the PED using the keyboard and the display, the user interface software enabling the user to select a mode of operation, including at least the following: a first mode that causes the PED to receive and store a reference signature from a remote computer, a second mode that causes the PED to receive and store a reference signature from a local environment associated with the PED, and at least one third mode that causes the PED to attempt to detect occurrence of an event that corresponds with a stored reference signature.

10. The PED of claim 9, wherein the PED comprises two third modes, one mode that causes the PED to identify the reference signature based upon a predefined correlation threshold that has been met and another mode that causes the PED to identify a reference signature that has the highest correlation.

11. A personal electronic device (PED) that can be transported with a user, comprising:

means for storing a reference signature;
means for detecting an event in an environment associated with the PED comprising:
  means for sensing a signal in the environment;
  means for correlating the signal with the reference signature; and
  means for indicating the detecting of the event based upon the correlating;
means for producing a notification upon the detecting of the event; and
means for enabling the PED to communicate with another PED and exchange information relating to detection of the event.

12. The PED of claim 11, further comprising a means for permitting the user to input whether or not the PED will communicate and exchange the information.

13. A system for sensory enhancement, comprising:
a plurality of personal electronic devices (PEDs);
means for communicating among the plurality of PEDs a selection of a reference signature corresponding to an event to be detected;
means for permitting one or more of the PEDs to measure a characteristic of an environment with a transducer associated therewith;
means for detecting the event in one or more of the PEDs; and
means for generating a notification signal in the one or more PEDs indicating detection of the event.

14. A method for a personal electronic device (PED) that can be transported with a user, comprising the steps of:
performing a first electronic based intelligence function; and
performing a second electronic based intelligence function, comprising:
  detecting an event in an environment to which the PED is exposed via a transducer by:
    storing a plurality of reference signatures having frequency domain characteristics;
    preprocessing a sensed signal by converting the sensed signal to a frequency domain signature; and
    determining when the sensed signal corresponds with one of the reference signatures by correlating the frequency domain signature with the plurality of reference signatures; and
  producing a notification upon detection of the event.

15. The method of claim 14, further comprising the steps of:
receiving an analog sensed signal; and
translating the analog sensed signal to one of the reference signatures via fast Fourier transform.

16. A method for a personal electronic device (PED) that can be transported with a user, comprising the steps of:
performing a first electronic based intelligence function; and
performing a second electronic based intelligence function, comprising:
  detecting an event in an environment to which the PED is exposed via a transducer by:
    storing a plurality of reference signatures having frequency domain characteristics;
    preprocessing a sensed signal by converting the sensed signal to a frequency domain signature; and
    determining when the sensed signal corresponds with one of the reference signatures by correlating the frequency domain signature with the plurality of reference signatures; and
  producing a notification upon detection of the event
wherein the event is a moving object in motion and further comprising the steps of:
  determining a Doppler shift associated with the moving object; and
  determining a proximity and speed of the moving object based upon the Doppler shift.

17. A method for a personal electronic device (PED) that can be transported with a user, comprising the steps of:
performing a first electronic based intelligence function; and
performing a second electronic based intelligence function, comprising:
  detecting an event in an environment to which the PED is exposed via at least two transducers;
  producing a notification upon detection of the event; and
  determining a direction associated with the event based upon signals sensed by the at least two transducers.

18. A method for a personal electronic device (PED) that can be transported with a user, comprising the steps of:
performing a first electronic based intelligence function; and
performing a second electronic based intelligence function, comprising:
  detecting an event in an environment to which the PED is exposed via a transducer;
  producing a notification upon detection of the event; and
  defining a range around the PED, inside of which the event may be detected and outside of which the event cannot be detected.

19. A method for a personal electronic device (PED) that can be transported with a user, comprising the steps of:
storing identification information relating to a plurality of events;
enabling the user to select an event from the stored identification information relating to the plurality of events;
storing reference signatures;
detecting the event in an environment associated with the PED by:
  sensing a signal in the environment;
  correlating the signal with a reference signature; and
  indicating the detecting of the event based upon the correlating; and producing a notification upon the detecting of the event.

20. A method for a personal electronic device (PED) that can be transported with a user, the PED having a computer based architecture with a keyboard, a display, and user interface software that enables the user of the PED to interact with the PED using the keyboard and the display, the method comprising the steps of:
storing a reference signature;
detecting an event in an environment associated with the PED by:
  sensing a signal in the environment;
  correlating the signal with the reference signature; and
  indicating the detecting of the event based upon the correlating;
producing a notification upon the detecting of the event;
enabling the user to store the reference signature with the user interface software; and
enabling the user to associate a picture with the reference signature with the user interface software.

21. A method for a personal electronic device (PED) that can be transported with a user, the PED having a computer based architecture with a keyboard, a display, one or more transducers for measuring environmental characteristics, and user interface software that enables the user of the PED to interact with the PED using the keyboard and the display, the method comprising the steps of:
- storing a reference signature;
- detecting an event in an environment associated with the PED by:
  - sensing a signal in the environment;
  - correlating the signal with the reference signature; and
  - indicating the detecting of the event based upon the correlating;
- producing a notification upon the detecting of the event;
- enabling the user to store the reference signature with the user interface software; and
- enabling the user of the PED to select with the user interface software which of the one or more transducers are to be operational by providing one or more inputs via the keyboard and receiving one or more outputs via the display.

22. A method for a personal electronic device (PED) that can be transported with a user, the PED having a computer based architecture with a keyboard, a display, and user interface software that enables the user of the PED to interact with the PED using the keyboard and the display, the method comprising the steps of:
- storing a reference signature;
- detecting an event in an environment associated with the PED by:
  - sensing a signal in the environment;
  - correlating the signal with the reference signature; and
  - indicating the detecting of the event based upon the correlating;
- producing a notification upon the detecting of the event;
- enabling the user to store the reference signature with the user interface software; and
- enabling the user to select with the user interface software a mode of operation, including at least the following: a first mode that causes the PED to receive and store a reference signature from a remote computer, a second mode that causes the PED to receive and store a reference signature from a local environment associated with the PED, and at least one third mode that causes the PED to attempt to detect occurrence of an event that corresponds with a stored reference signature.

23. The method of claim 22, wherein the PED includes two third modes, one mode that causes the PED to identify the reference signature based upon a predefined correlation threshold that has been met and another mode that causes the PED to identify a reference signature that has the highest correlation.

24. A method for a personal electronic device (PED) that can be transported with a user, comprising the steps of:
- storing a reference signature;
- detecting an event in an environment associated with the PED by:
  - sensing a signal in the environment;
  - correlating the signal with the reference signature; and
  - indicating the detecting of the event based upon the correlating;
- producing a notification upon the detecting of the event; and
- enabling the PED to communicate with another PED and exchange information relating to detecting of the event.

25. The method of claim 24, further comprising the step of permitting the user to input whether or not the PED will communicate and exchange the information.

26. A method for a sensory enhancement, comprising the steps of:
- providing a plurality of personal electronic devices (PEDs);
- enabling communication of a selection of a reference signature corresponding to an event to be detected among the plurality of PEDs;
- enabling one or more of the PEDs to measure a characteristic of an environment with a transducer associated therewith;
- enabling detection of the event in one or more of the PEDs; and
- enabling a notification signal to be generated in the one or more PEDs indicating detection of the event.

* * * * *

UNITED STATES PATENT AND TRADEMARK OFFICE
CERTIFICATE OF CORRECTION

| | | |
|---|---|---|
| PATENT NO. | : 7,872,574 B2 | Page 1 of 1 |
| APPLICATION NO. | : 11/345058 | |
| DATED | : January 18, 2011 | |
| INVENTOR(S) | : William L. Betts et al. | |

It is certified that error appears in the above-identified patent and that said Letters Patent is hereby corrected as shown below:

Column 21, line 51, delete "indicting" and insert --indicating--.

Column 21, line 64, delete "indicting" and insert --indicating--.

Column 22, line 18, delete "indicting" and insert --indicating--.

Column 22, line 41, delete "indicting" and insert --indicating--.

Signed and Sealed this
Thirteenth Day of March, 2012

David J. Kappos
*Director of the United States Patent and Trademark Office*